US008981293B2

(12) United States Patent
Gong et al.

(10) Patent No.: US 8,981,293 B2
(45) Date of Patent: Mar. 17, 2015

(54) SYSTEM FOR INSPECTING FLAT PANEL DISPLAY USING SCANNING ELECTRON MICROSCOPE

(71) Applicant: Samsung Display Co., Ltd., Yongin, Gyeonggi-Do (KR)

(72) Inventors: Dong-Hyun Gong, Yongin (KR); Young-Gil Park, Yongin (KR); Jae-Kwon Lee, Yongin (KR); Jung-Un Kim, Yongin (KR); Do-Soon Jung, Suwon-si (KR); Hyun-Jung Kim, Yongin-si (KR); Geum-Tae Kim, Osan-si (KR)

(73) Assignee: Samsung Display Co., Ltd. (KR)

( * ) Notice: Subject to any disclaimer, the term of this patent is extended or adjusted under 35 U.S.C. 154(b) by 0 days.

(21) Appl. No.: 14/199,906

(22) Filed: Mar. 6, 2014

(65) Prior Publication Data

US 2014/0291514 A1 Oct. 2, 2014

(30) Foreign Application Priority Data

Mar. 26, 2013 (KR) ........................ 10-2013-0032294

(51) Int. Cl.
*H01J 37/28* (2006.01)
*H01J 37/301* (2006.01)
(Continued)

(52) U.S. Cl.
CPC .............. *H01J 37/261* (2013.01); *G01N 21/88* (2013.01)
USPC ........... 250/310; 250/307; 250/306; 250/309; 250/311; 250/396 R; 250/492.3; 356/364; 356/369

(58) Field of Classification Search
CPC ........... H01J 37/28; H01J 37/20; H01J 37/16; H01J 37/18; H01J 37/301; H01J 37/228; H01J 37/256; H01J 37/3056; G03F 7/70916; G03F 7/70933
USPC ............. 250/306, 307, 310, 311, 309, 396 R, 250/492.3; 356/364, 369
See application file for complete search history.

(56) References Cited

U.S. PATENT DOCUMENTS 7,230,257 B2 * 6/2007 Uchida ..................... 250/492.22
7,359,052 B2 * 4/2008 Fielden et al. ................. 356/369
7,564,552 B2 * 7/2009 Fielden et al. ................. 356/364

(Continued)

FOREIGN PATENT DOCUMENTS

KR 10-2004-0076734 A 9/2004
KR 10-2005-0088416 A 9/2005

(Continued)

*Primary Examiner* — David A Vanore
(74) *Attorney, Agent, or Firm* — Knobbe, Martens, Olson & Bear LLP

(57) ABSTRACT

An inspection system includes: an automated optical inspection device detecting a defect of an inspection object by using a light; a scanning electron microscope device for inspecting the defect of the inspection object by using an electron beam and including a vacuum chamber; a stage positioned below and spaced from the scanning electron microscope device and supporting the inspection object; and a transferring device connected to the scanning electron microscope chamber and the automated optical inspection and transferring the scanning electron microscope device and the automated optical inspection device to positions over the stage. Air is in a gap between the chamber and the inspection object. Accordingly, an inspection object of a large size may be inspected for analysis without damage to the inspection object.

14 Claims, 6 Drawing Sheets

(51) Int. Cl.
*H01J 37/26* (2006.01)
*G01N 21/88* (2006.01)

(56) References Cited

U.S. PATENT DOCUMENTS

| | | | |
|---|---|---|---|
| 7,586,093 B2* | 9/2009 | Feuerbaum | 250/311 |
| 7,764,376 B2* | 7/2010 | Fielden et al. | 356/364 |
| 8,164,057 B2* | 4/2012 | Shachal | 250/307 |
| 8,492,716 B2* | 7/2013 | Shachal et al. | 250/311 |
| 2004/0046120 A1* | 3/2004 | Moses et al. | 250/311 |
| 2009/0279088 A1* | 11/2009 | Fielden et al. | 356/364 |
| 2010/0140470 A1* | 6/2010 | Shachal | 250/307 |
| 2010/0245790 A1* | 9/2010 | Seltmann et al. | 355/30 |
| 2011/0168889 A1* | 7/2011 | Shachal et al. | 250/307 |
| 2011/0210247 A1* | 9/2011 | Shachal et al. | 250/307 |
| 2012/0241608 A1* | 9/2012 | Shachal | 250/307 |
| 2013/0284923 A1* | 10/2013 | Hatano et al. | 250/310 |
| 2013/0313430 A1* | 11/2013 | Ominami et al. | 250/307 |
| 2013/0320211 A1* | 12/2013 | Park et al. | 250/310 |
| 2014/0117232 A1* | 5/2014 | Shachal et al. | 250/307 |

FOREIGN PATENT DOCUMENTS

| | | |
|---|---|---|
| KR | 10-2007-0087407 A | 8/2007 |
| KR | 10-2009-0116554 A | 11/2009 |
| KR | 10-2011-0073318 A | 6/2011 |
| KR | 10-2011-0076934 A | 7/2011 |
| KR | 10-2012-0041587 A | 5/2012 |

* cited by examiner

SYSTEM FOR INSPECTING FLAT PANEL DISPLAY USING SCANNING ELECTRON MICROSCOPE

RELATED APPLICATIONS

This application claims priority to and the benefit of Korean Patent Application No. 10-2013-0032294 filed in the Korean Intellectual Property Office on Mar. 26, 2013, the entire contents of which are incorporated herein by reference.

BACKGROUND

1. Field

The described technology relates generally to an inspection system using a scanning electron microscope.

2. Description of the Related Art

In general, flat panel displays such as a liquid crystal display (LCD) and an organic light emitting diode (OLED) display are formed by depositing a plurality of thin films and wires. To inspect for existence of impurities or particles on the thin film of the flat panel display, or a short circuit of the wires, an inspection system using an automatic optical inspection (AOI) unit or a vacuum scanning electron microscope (SEM) is used.

The automated optical inspection photographs an inspection object by using an optical system to determine defect existence of the inspection object. However, the automated optical inspection only determines the defect existence of the inspection object, and cannot confirm a cause of the defect such that the cause of the defect must be analyzed by the vacuum scanning electron microscope.

The vacuum scanning electron microscope (SEM) is limited to a size of the inspection object to be observed by a size limitation of a vacuum chamber. A vacuum scanning electron microscope that is capable of observing a semiconductor wafer of up to 30 inches has been developed, however usage of the vacuum scanning electron microscope is difficult for a flat panel display of a size from 730×920 mm to 2200×2500 mm because of the size limitation of the vacuum chamber such that the inspection object is analyzed after cutting it.

In a case of increasing the size of the vacuum chamber to be applied to the flat panel display, secondary electrons (SE) or back-scattered electrons (BSE) from an inspection object positioned in the vacuum chamber cause interference by a charging effect generated in the vacuum chamber such that image observation of the inspection object is difficult, and carbon contamination by a hydrocarbon compound (HxCx) may be generated due to a pump used for the vacuum chamber.

Also, after confirming defect existence of the inspection object by using the automated optical inspection, the inspection object is moved to the vacuum scanning electron microscope to analyze the defect cause such that the inspection process is complicated, and the inspection object must be cut before using the vacuum scanning electron microscope such that the inspection process is more complicated, and furthermore, the automated optical inspection and the vacuum scanning electron microscope must be separately installed such that a space occupied by the inspection system is increased and manufacturing cost is increased.

Also, the automated optical inspection is sensitive to external vibration such that detection power is limited.

The above information disclosed in this Background section is only for enhancement of understanding of the background of the described technology and therefore it may contain information that does not form the prior art that is already known in this country to a person of ordinary skill in the art.

SUMMARY

One aspect of the present invention provides an inspection system using a scanning electron microscope for performing an inspection of an inspection object placed outside a vacuum chamber and in the atmosphere without a limitation of a size of the inspection object.

An inspection system using a scanning electron microscope according to an exemplary embodiment includes: an automated optical inspection device for detecting defect of an inspection object by using a light; a scanning electron microscope device for inspecting the defect of the inspection object by using an electron beam and comprising a vacuum chamber; a stage positioned below and spaced from the scanning electron microscope device and supporting the inspection object; and a transferring device connected to the scanning electron microscope device and the automated optical inspection device and transferring the scanning electron microscope and the automated optical inspection device to positions over the stage, wherein air is in a gap between the chamber and the inspection object.

An optical microscope attached to the scanning electron microscope device and irradiating light to the inspection object to inspect the inspection object may be further included.

The defect existence of the inspection object may be confirmed through the automated optical inspection device, a first defect cause analyzing test of the inspection object may be performed through the optical microscope, and a secondary detailed defect cause analyzing test of the inspection object may be performed through the scanning electron microscope device.

The scanning electron microscope device may include: the vacuum chamber; a scanning electron microscope positioned inside the vacuum chamber and scanning the electron beam to the inspection object; and a signal detector positioned inside the vacuum chamber and detecting a signal from the inspection object.

The signal detector may include a secondary electron detector detecting secondary electrons from the inspection object, a back-scattered electron detector detecting back-scattered electrons from the inspection object; and a characteristic X-ray detector detecting characteristic X-rays from the inspection object.

The chamber may further include a membrane, and the membrane may allow the electron beam from the scanning electron microscope to pass therethrough and further configured to allow the secondary electrons, the back-scattered electrons, and the characteristic X-rays from the inspection object to pass therethrough such that the secondary electrons, the back-scattered electrons, and the characteristic X-rays from the inspection object may be transferred inside the chamber.

A flatness device connected to the stage and adjusting flatness of the stage may be further included.

An interval control device connected to the scanning electron microscope device and adjusting a distance between the chamber and the inspection object may be further included.

A membrane particle inspection and removing device performing particle inspection and particle removal of the membrane may be further included.

The membrane particle inspection and removing device may perform the particle inspection and the particle removal from the membrane before the inspection of the inspection object using the scanning electron microscope device.

A supporting plate supporting the stage and the transferring device may be further included, and the membrane particle inspection and removing device is installed on the supporting plate.

A first vibration control device installed below the supporting plate and measuring and eliminating external vibration to prevent an influence by the external vibration on the scanning electron microscope device may be further included.

The transferring device may include a fixing part fixed to the supporting plate, a transferring part transferring along the fixing part and support the scanning electron microscope device and the automated optical inspection device, and a second vibration control device installed between the fixing part and the transferring part.

A cover frame at least partly enclosing the scanning electron microscope device, the stage, and the transferring device and blocking magnetism and noise to inhibit the magnetism and noise from affecting the scanning electron microscope device may be further included.

According to embodiments of the present invention, by using the inspection system including the automated optical inspection device, the scanning electron microscope device, and the optical microscope connected thereto, determining defect existence of the inspection object, capturing the optical image of the particle generated in the inspection object, gleaning 3-D information of the inspection object, and component analysis may be simultaneously performed, thereby reducing the inspection time.

Also, the automated optical inspection device, the scanning electron microscope device, and the optical microscope connected thereto are installed to the transferring device such that they may be moved to a predetermined position on the inspection object. Thus, the size of the inspection object is not limited.

Further, a typical vacuum scanning electron microscope has a vacuum chamber with a limited size and an object is placed in the vacuum chamber, and thus, inspection of an inspection object of a large size such as a flat panel display is difficult. But, according to embodiments of the present invention, the inspection object is placed in the atmosphere and air is in a gap between the chamber of the scanning electron microscope device and the inspection object. Thus, the inspection of an inspection object of a large size is possible, thereby the shape, the component, the structure, etc., of the inspection object of a large size may be observed and analyzed.

Accordingly, according to embodiments of the present invention, an inspection object of a large size may be inspected for the analysis without damage to the inspection object such that a cost reduction and a yield improvement may be realized.

In addition, the inspection object is positioned in the atmosphere such that image distortion of the inspection object which would be caused by the charging effect generated in the vacuum chamber can be avoided or minimized and the inspection object is not contaminated by carbon, thereby realizing correct inspection.

As described, according to the characteristic of the scanning electron microscope that is sensitive to external noise such as external vibration, magnetism, and noise, the flatness device and the variation control device are installed to the inspection system such that the influence of the external noise on the inspection system may be minimized.

Also, by installing the vibration control device, the vibration affecting the automated optical inspection and the scanning electron microscope device may be minimized and the detection power of the automated optical inspection device that is sensitive to the external vibration may be improved.

DETAILED DESCRIPTION

Figure 1:
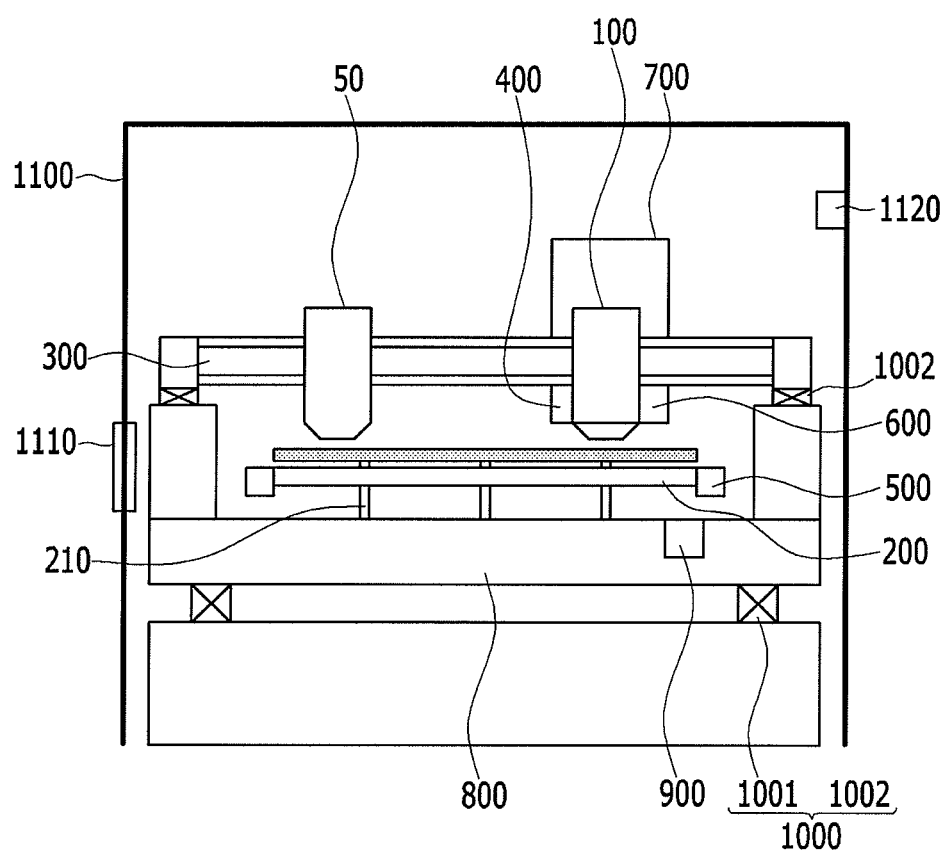
FIG. 1 is a schematic diagram of an inspection system using a scanning electron microscope according to an exemplary embodiment.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Descriptions of parts not related to the present invention are omitted, and like reference numerals designate like elements throughout the specification.

Thus, an inspection system of a scanning electron microscope according to an exemplary embodiment will be described with reference to FIG. 1 to FIG. 6.

Figure 2:
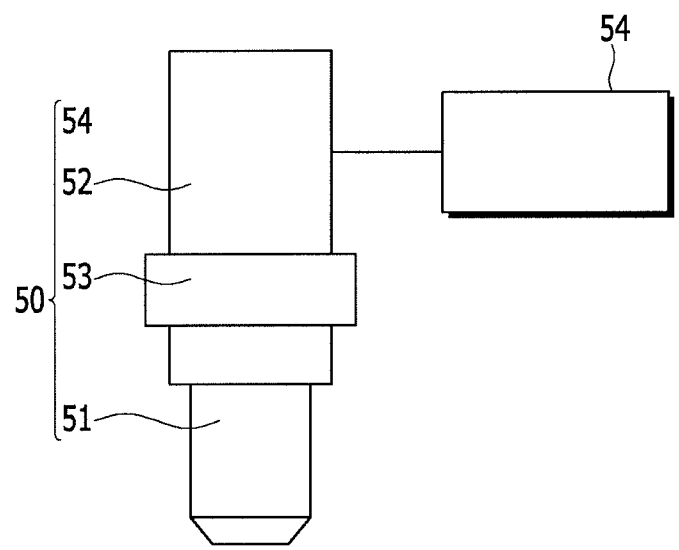
FIG. 2 is a schematic diagram of an automated optical inspection device of an inspection system using a scanning electron microscope according to an exemplary embodiment.
Figure 3:
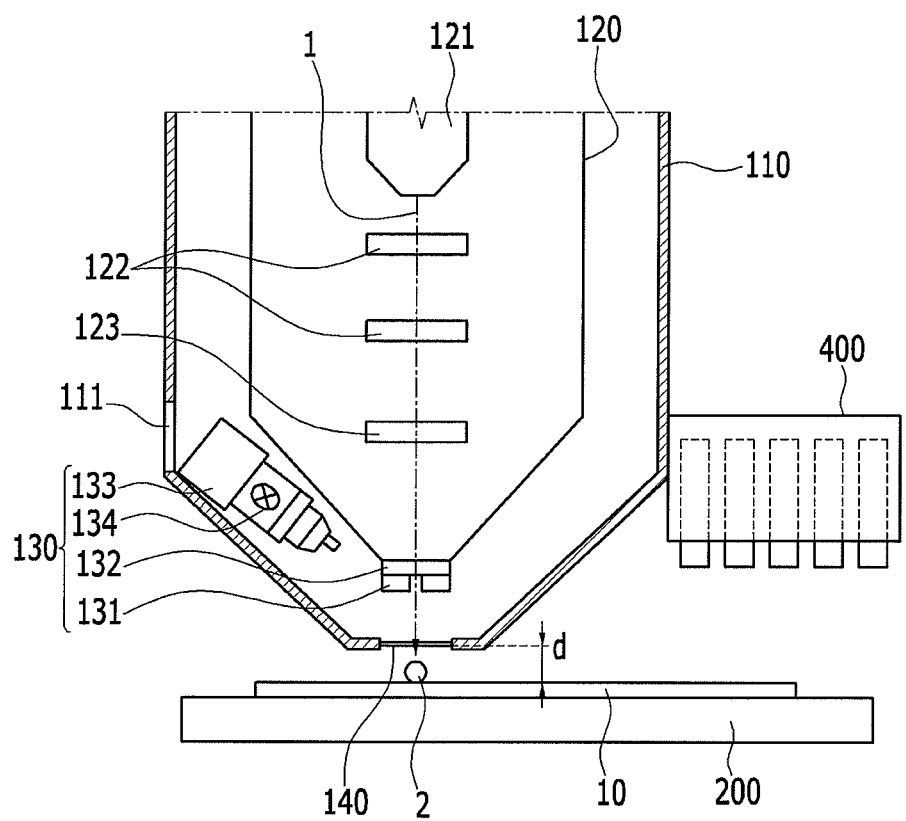
FIG. 3 is an enlarged view of a scanning electron microscope device and a stage of an inspection system using a scanning electron microscope according to an exemplary embodiment.
Figure 4:
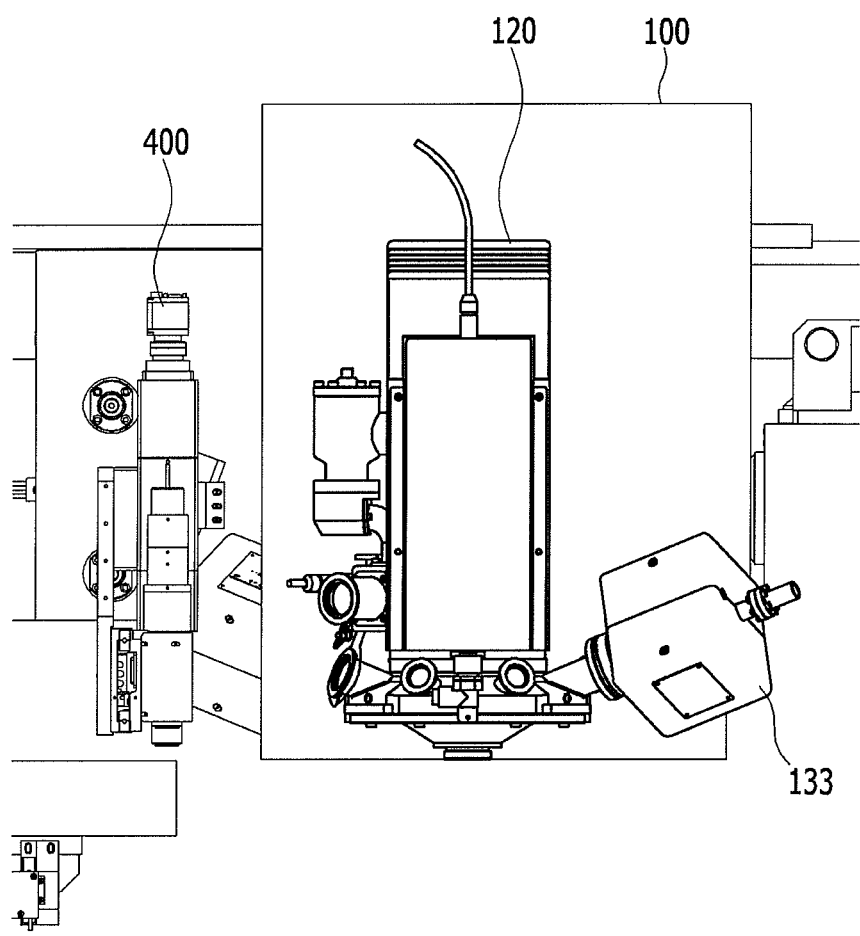
FIG. 4 is a detailed view of a scanning electron microscope device of an inspection system using a scanning electron microscope according to an exemplary embodiment.
Figure 5:
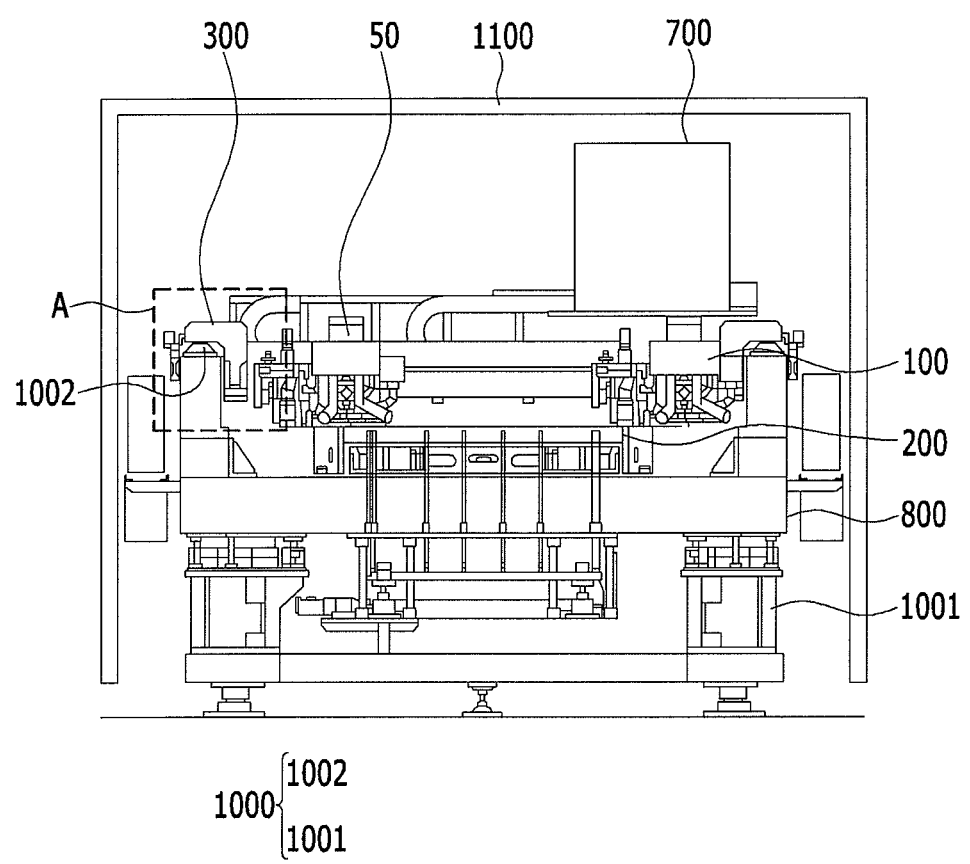
FIG. 5 is a lateral view of an inspection system using a scanning electron microscope according to an exemplary embodiment.
Figure 6:
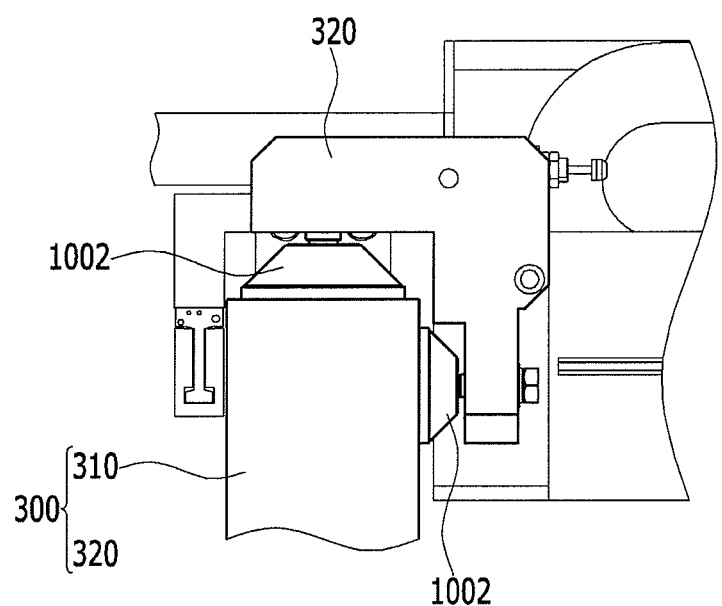
FIG. 6 is an enlarged view of a portion A of FIG. 5.

FIG. 1 is a schematic diagram of an inspection system using a scanning electron microscope according to an exemplary embodiment, FIG. 2 is a schematic diagram of an automated optical inspection of an inspection system using a scanning electron microscope according to an exemplary embodiment, FIG. 3 is an enlarged view of a scanning electron microscope device and a stage of an inspection system using a scanning electron microscope according to an exemplary embodiment, FIG. 4 is a detailed view of a scanning electron microscope device of an inspection system using a scanning electron microscope according to an exemplary embodiment, FIG. 5 is a lateral view of an inspection system using a scanning electron microscope according to an exemplary embodiment, and FIG. 6 is an enlarged view of a portion A of FIG. 5.

As shown in FIG. 1 to FIG. 6, an inspection system using a scanning electron microscope according to an exemplary embodiment includes an automated optical defect detector or optical inspection device 50 for inspecting defect existence of an inspection object 10 or detecting one or more defects of the inspection object 10 by using a light, a scanning electron microscope device 100 for scanning an electron beam 1 to the inspection object 10 to inspect the inspection object 10, a stage 200 spaced from and disposed below the scanning electron microscope device 100 and the automated optical inspection device 50 and supporting the inspection object 10 thereon, and a transferring device 300 transferring the scanning electron microscope device 100 and the automated optical inspection device 50 on the stage 200. The transferring device 300 is connected to the scanning electron microscope device 100 and the automated optical inspection device 50. In embodiments, the inspection object 10 may be a flat panel display, such as a liquid crystal display (LCD) and an organic light emitting diode (OLED) display, which is to be or being subject to inspection.

As shown in FIG. 2, the automated optical inspection device 50 includes a lens 51, a camera 52 photographing an image of the inspection object 10 transmitted through the lens 51, a barrel 53 connecting the lens 51 and the camera 52, and a controller 54 reading a defect existence by obtaining the image photographed by the camera 52 and comparing the image with a reference pattern. The automated optical inspection device 50 may quickly read out the defect existence of the inspection object 10.

As shown in FIG. 3, the scanning electron microscope device 100 includes a vacuum chamber 110 maintaining a vacuum condition, a scanning electron microscope 120 positioned inside the vacuum chamber 110 and scanning the electron beam 1 to the inspection object 10, and a signal detector 130 positioned inside the vacuum chamber 110 and detecting a signal from the inspection object 10. As described, the scanning electron microscope 120 and the signal detector 130 maintain the vacuum condition inside the scanning electron microscope device 100.

The scanning electron microscope 120 includes an electron gun 121 emitting the electron beam 1, an electromagnetic lens 122 such as a condenser lens and an objective lens controlling a progressing direction of the electron beam 1, and an aperture 123 controlling an amount of the progressing electron beam 1.

The signal detector 130 includes a secondary electron detector 131 detecting secondary electrons (SE) emitted from the inspection object 10 by the electron beam 1 scanned to the inspection object 10, a back-scattered electron detector 132 detecting back-scattered electrons (BSE) from the inspection object 10, and a characteristic X-ray detector 133 detecting a characteristic X-ray from the inspection object 10. The image of the inspection object 10 and components thereof may be measured and analyzed by using the signal detector 130.

The secondary electron detector 131 and the back-scattered electron detector 132 are attached below the scanning electron microscope 120, and the characteristic X-ray detector 133 is obliquely installed to the side surface of the scanning electron microscope 120. The characteristic X-ray detector 133 detects the inspection object 10 positioned in the atmosphere rather than in a vacuum chamber 110 and the characteristic X-ray generated by the reaction of the electron beam 1 to analysis the components of the inspection object 10. To minimize influence of the characteristic X-ray detector 133 on the scanning electron microscope 120, an angle of the characteristic X-ray detector 133 may be controlled or the characteristic X-ray detector 133 may be carried in the scanning electron microscope device 100. For this, an angle controller 134 may be installed to the characteristic X-ray detector 133 or a characteristic X-ray detector carry-out door 111 may be installed to the scanning electron microscope device 100.

A membrane 140 is installed under the scanning electron microscope device 100. The membrane 140 is formed of a non-conductive material including carbon (C), nitrogen (N), oxygen (O), or silicon (Si) and a material having transmittance and low absorption such that the electron beam 1, the secondary electrons, the back-scattered electrons, and the characteristic X-rays are not absorbed but are transmitted. In the membrane 140 made of carbon (C) and having excellent transmittance, the thickness may be in a range of about 10 nm to about 3 μm, and in this case, the transmittance of the membrane 140 is in a range of 90% to 100%. When the thickness of the membrane 140 is in a range of about 10 nm to about 3 μm, the risk of damages by a physical impact can be minimized, and absorption of the electron beam can be minimized such that the transmittance can be maintained 90% to 100%. Thus, the inspection can be appropriately performed.

This membrane 140 maintains the vacuum condition of the scanning electron microscope device 100, and the electron beam 1 scanned in the scanning electron microscope 120 is simultaneously passed and may be irradiated to the inspection object 10. Also, detecting signals of the secondary electrons, the back-scattered electrons, and the characteristic X-rays from the inspection object 10 are sent inside the scanning electron microscope device 100 such that they are transmitted to the secondary electron detector 131, the back-scattered electron detector 132, and the characteristic X-ray detector 133. Therefore, the membrane 140 allows air to be in a space d between the scanning electron microscope device 100 and the inspection object 10. Accordingly, while a conventional vacuum scanning electron microscope 120 is limited to the size of the vacuum chamber 110 such that inspection of an inspection object 10 of a large size such as a flat panel display is difficult, according to the present invention, air is in a gap between the chamber 110 of the scanning electron microscope device 100 and the inspection object 10 such that an inspection object 10 of a large size can be placed outside the vacuum chamber, i.e. in a room or the atmosphere, and thereby the shape, the components, the structure, etc., of the inspection object 10 of a large size may be observed and analyzed;

Accordingly, the inspection object 10 with a large size may be inspected for the analysis without damage to the inspection object 10 such that a cost reduction and a yield improvement may be obtained.

Also, the inspection object 10 is positioned in the atmosphere such that image distortion of the inspection object 10 by the charging effect generated in the vacuum chamber 110 is prevented and the inspection object 10 is not contaminated by carbon, thereby realizing correct inspection.

An optical microscope 400 is attached to the scanning electron microscope device 100, and irradiates light to the inspection object 10 to inspect the existence of a particle 2 attached to the surface of the inspection object 10. As described, the optical microscope 400 is attached to the scanning electron microscope device 100 such that it is simultaneously moved with the scanning electron microscope device 100 by the transferring device 300.

The possible maximum magnification of an optical microscope 400 is about 100 times, and the possible magnification in a scanning electron microscope device 100 is about a million times such that resolution of the scanning electron microscope device 100 of several nanometers is possible.

Accordingly, the defect existence of the inspection object 10 is determined through an automated optical defect detector 50 first defect cause analyzing test of the inspection object 10 having the defect that may be performed through the optical microscope 400 and a secondary detailed defect cause analyzing test of the inspection object 10 may be performed through the scanning electron microscope device 100 to obtain information on the shape, the size, and the component of the particle.

As described, the inspection system using the scanning electron microscope according to an exemplary embodiment includes the automated optical inspection device 50, the scanning electron microscope device 100, and the optical microscope 400 connected thereto such that the defect existence of the inspection object 10, the optical image of the particle from the inspection object 10 having the defect, the 3-D information of the inspection object 10, and the component analysis may be simultaneously performed.

The stage 200 may be moved in X-axis, Y-axis, and Z-axis directions to inspect the entire region of the inspection object 10, and the transferring device 300 may also be moved in the X-axis, Y-axis, and Z-axis directions to inspect the entire region of the inspection object 10. The stage 200 is installed with a left pin 210 to receive the inspection object 10 from the transferring robot.

The automated optical detector 50, the scanning electron microscope device 100, and the optical microscope 400 attached thereto are connected to the transferring device 300 such that the optical test using the automated optical inspection device 50 and the microscope test using the scanning electron microscope device 100 and the optical microscope 400 may be quickly performed, and the scanning electron microscope 120 and the optical microscope 400 may be simultaneously moved to a predetermined position over the inspection object 10 such that the size of the inspection object 10 is not limited.

The stage 200 is installed with a flatness device 500 controlling flatness of the stage 200. A plurality of flatness devices 500 may be installed to the stage 200, and the flatness device 500 measures the flatness of the stage 200 to control the flatness such that a physical collision between the scanning electron microscope device 100 and the inspection object 10 is prevented.

The scanning electron microscope device 100 is attached with an interval control device 600, and the interval control device 600 measures a distance d between the scanning electron microscope device 100 and the inspection object 10 in real time by using a laser sensor and feeds a signal back to the transferring device 300 to control the position of the scanning electron microscope device 100, and thereby the physical collision between the scanning electron microscope device 100 and the inspection object 10 is prevented.

In the conventional art, the distance d between the lower portion of the scanning electron microscope device 100 and the inspection object 10 may be closer to a millimeter degree, however the inspection system using the scanning electron microscope according to an exemplary embodiment ma y close the distance d between the membrane 140 of the scanning electron microscope device 100 and the inspection object 10 to the micrometer degree by using the flatness device 500 and the interval control device 600 such that analysis extent of the inspection object 10 may be improved.

As described, the transferring device 300 is installed together with the automated optical inspection device 50, the scanning electron microscope device 100, the optical microscope 400, and the interval control device 600 such that the automated optical inspection device 50, the scanning electron microscope device 100, the optical microscope 400, and the interval control device 600 may be integrally moved by the transferring device 300. Accordingly, the automated optical inspection device 50, the scanning electron microscope device 100, the optical microscope 400, and the interval control device 600 are simultaneously moved to all inspection positions of the inspection object 10 by using the transferring device 300 without limitation of the size of the inspection object 10, thereby performing the inspection process.

An electronic control device 700 to control the electronic devices inside the scanning electron microscope device 100 is installed to the transferring device 300.

A supporting plate 800 supporting the stage 200 and the transferring device 300 is installed, and a membrane particle inspection and removing device 900 is installed on the supporting plate 800. The membrane particle inspection and removing device 900 performs the inspection and removal of the particle attached to the surface of the membrane 140 before the inspection of the inspection object 10 using the scanning electron microscope device 100. Accordingly, the inspection for the inspection object 10 being incompletely performed because of the particle attached to the surface of the membrane 140 may be prevented.

Also, a vibration control device 1000 to minimize vibration is installed in the inspection system. The variation control device 1000 includes a first variation control device 1001 removing external vibration and a second variation control device 1002 minimizing vibration of the transferring device 300.

The first variation control device 1001 is installed under the supporting plate 800, and measures and removes the external vibration such that an influence by the external vibration on the scanning electron microscope device 100 may be prevented. In the atmosphere, the microscope device 100 is influenced by the external vibration, however in an exemplary embodiment, by installing the first vibration control device 1001, the influence of the external vibration on the scanning electron microscope device 100 may be minimized.

As shown in FIG. 1, FIG. 5, and FIG. 6, the second variation control device 1002 is installed between a fixing part 310 and a transferring part 320 of the transferring device 300 and generates an air gap between the transferring part 320 and the fixing part 310 when the transferring part 320 is moved on the surface of the fixing part 310, and thereby the transferring part 320 may be horizontally moved without friction. Accordingly, the vibration affecting the automated optical inspection device 50 and the scanning electron microscope device 100 connected to the transferring part 320 may be minimized, and the detection power of the automated optical inspection device 50 that is sensitive to external vibration may be improved.

A cover frame 1100 entirely enclosing the scanning electron microscope device 100, the stage 200, and the transferring device 300 is installed. The cover frame 1100 is formed of a blocking material such as aluminum (Al) or permalloy such that external magnetism and noise generated in surrounding devices or surrounding wires is prevented from being transmitted to the scanning electron microscope device 100 such that the magnetism and the noise do not affect the scanning electron microscope device 100. The cover frame 1100 may be installed with a cover door 1110 for passing the inspection object 10 through for it to be loaded and unloaded to and from the stage 200. As described, by installing the cover door 1110, when performing the inspection process for the inspection object 10, the cover door 1110 is closed such that the scanning electron microscope device 100 is completely shielded from the external magnetism and noise.

Also, a magnetic sensor 1120 is installed inside the cover frame 1100 such that the influence of the magnetism on the scanning electron microscope 120 may be minimized. Accordingly, the analysis force for the inspection object 10 of the scanning electron microscope device 100 may be improved.

As described, according to the characteristics of the scanning electron microscope 120 that is sensitive to external noise such as external vibration, magnetism, and noise, the flatness device 500 and the variation control device 1000 are installed to the inspection system in the atmosphere to inspect the inspection object 10 such that the influence of the external noise on the inspection system may be minimized.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of Symbols>

1: electron beam
10: inspection object
50: automated optical inspection device
100: scanning electron microscope device
200: stage
300: transferring device
400: optical microscope
500: flatness device
600: interval control device
700: electron control device
800: supporting plate
1000: variation control device

What is claimed is:

1. An inspection system comprising:
   an automated optical inspection device configured to detect a defect of an inspection object by using a light;
   a scanning electron microscope device configured to inspect the defect of the inspection object by using an electron beam and comprising a vacuum chamber;
   a stage positioned below and spaced from the scanning electron microscope device and configured to support the inspection object; and
   a transfer device connected to the scanning electron microscope device and the automated optical inspection device and configured to transfer the scanning electron microscope device and the automated optical inspection device to positions over the stage,
   wherein air is in a gap between the chamber and the inspection object.

2. The inspection system of claim 1, further comprising:
   an optical microscope attached to the chamber of the scanning electron microscope device and configured to irradiate light to the inspection object to inspect the inspection object.

3. The inspection system of claim 2, wherein the automated optical inspection device is configured to confirm the defect of the inspection object, wherein the optical microscope is configured to conduct a first observation of the defect of the inspection object, wherein the scanning electron microscope device is configured to conduct a secondary detailed cause observation of the defect of the inspection object.

4. The inspection system of claim 2, wherein the scanning electron microscope devices comprises:
   the vacuum chamber;
   a scanning electron microscope positioned inside the vacuum chamber and configured to scan the electron beam to the inspection object; and
   a signal detector positioned inside the vacuum chamber and configured to detect a signal from the inspection object.

5. The inspection system of claim 4, wherein the signal detector comprises:
   a secondary electron detector configured to detect secondary electrons from the inspection object;
   a back-scattered electron detector configured to detect back-scattered electrons from the inspection object; and
   a characteristic X-ray detector configured to detect characteristic X-rays from the inspection object.

6. The inspection system of claim 5, wherein the chamber further comprising:
   a membrane configured to allow the electron beam from the scanning electron microscope to pass therethrough and further configured to allow the secondary electrons, the back-scattered electrons, and the characteristic X-rays from the inspection object to pass therethrough such that the secondary electrons, the back-scattered electrons, and the characteristic X-rays from the inspection object are transferred inside the chamber.

7. The inspection system of claim 2, further comprising:
   a flatness device connected to the stage and configured to adjust flatness of the stage.

8. The inspection system of claim 7, further comprising:
   an interval control device connected to the scanning electron microscope device and configured to adjust a distance between the chamber and the inspection object.

9. The inspection system of claim 6, further comprising:
   a membrane particle inspection and removing device configured to perform particle inspection and particle removal of the membrane.

10. The inspection system of claim 9, wherein the membrane particle inspection and removing device configured to perform the particle inspection and remove the particle from the membrane before the inspection of the inspection object using the scanning electron microscope device.

11. The inspection system of claim 10, further comprising:
    a supporting plate configured to support the stage and the transfer device, wherein the membrane particle inspection and removing device is installed on the supporting plate.

12. The inspection system of claim 11, further comprising:
    a first vibration control device installed below the supporting plate and configured to measure and eliminate external vibration to minimize or avoid an influence on the scanning electron microscope device by the external vibration.

13. The inspection system of claim 11, wherein the transfer device comprises:
    a fixing part fixed to the supporting plate;
    a transfer part configured to transfer along the fixing part and support the scanning electron microscope device and the automated optical inspection device; and
    a second vibration control device installed between the fixing part and the transfer part.

14. The inspection system of claim 11, further comprising:
    a cover frame at least partly enclosing the scanning electron microscope device, the stage, and the transfer device and configured to block magnetism and noise to inhibit the magnetism and the noise from affecting the scanning electron microscope device.

* * * * *